United States Patent [19]
Weathers

[11] Patent Number: 5,725,472
[45] Date of Patent: Mar. 10, 1998

[54] PSYCHOTHERAPY APPARATUS AND METHOD FOR THE INPUTTING AND SHAPING NEW EMOTIONAL PHYSIOLOGICAL AND COGNITIVE RESPONSE PATTERNS IN PATIENTS

[76] Inventor: Lawrence R. Weathers, West 1525-8th Ave., Spokane, Wash. 99204

[21] Appl. No.: 574,196

[22] Filed: Dec. 18, 1995

[51] Int. Cl.$^6$ .................................................. A61G 10/00
[52] U.S. Cl. .......................... 600/21; 600/27; 128/732; 128/905
[58] Field of Search ................... 600/21, 26–28; 128/731–732, 897–898, 905

[56] References Cited

U.S. PATENT DOCUMENTS

| | | | |
|---|---|---|---|
| 3,014,477 | 12/1961 | Carlin | 128/1 |
| 3,826,250 | 7/1974 | Adams | 128/24.2 |
| 4,893,615 | 1/1990 | Khabirova | 128/24.2 |
| 5,024,650 | 6/1991 | Hagiwara et al. | 600/26 |
| 5,219,322 | 6/1993 | Weathers | 600/27 |
| 5,266,070 | 11/1993 | Hagiwara et al. | 600/27 |
| 5,387,178 | 2/1995 | Moses | 600/27 |

FOREIGN PATENT DOCUMENTS

| | | |
|---|---|---|
| 4-348763 | 12/1992 | Japan. |
| 1648486 | 5/1991 | U.S.S.R. |
| 2201599 | 9/1988 | United Kingdom. |
| WO8800480 | 1/1988 | WIPO. |

*Primary Examiner*—John P. Lacyk
*Attorney, Agent, or Firm*—Flanagan & Flanagan

[57] ABSTRACT

A psychotherapy apparatus and method for inputting and shaping new emotional, physiological and cognitive response patterns in a patient includes an enclosure for isolating a patient from external stimuli, lights and earphones for respectively generating and presenting visual and auditory stimuli to the patient, an air flow delivery tube, an air flow fan for delivering a flow of air to the patient for inhalation by the patient, an electro-thermal heat pump coupled to the tube and fan being operable for controlling the temperature of the flow of air delivered to and inhaled by the patient to thereby control the temperature of the patient's hypothalamus, and a flow control valve between the heat pump and tube and being operable to control the proportion of heated and cooled air entering the tube. The apparatus also includes a computer-implemented expert system for developing a patient's treatment program and for coordinating and timing the occurrence of the visual and auditory stimuli and the controlling of the temperature of the flow of air delivered to and inhaled by the patient so as to operate the same in a desired predetermined coordinated fashion as determined by the patient's treatment program.

24 Claims, 4 Drawing Sheets

PSYCHOTHERAPY APPARATUS AND METHOD FOR THE INPUTTING AND SHAPING NEW EMOTIONAL PHYSIOLOGICAL AND COGNITIVE RESPONSE PATTERNS IN PATIENTS

BACKGROUND OF THE INVENTION

1. Field of the Invention

The present invention generally relates to psychotherapy techniques and, more particularly, to psychotherapy apparatus and method for inputting and shaping new emotional, physiological and cognitive response patterns in a patient through restricting, selecting, controlling and focusing the kinds of stimuli reaching the patient.

2. Description of the Prior Art

Many members of society currently demonstrating various undesirable (both pathological and non-pathological) behaviors are burdened with various emotional problems and emotionally-aggravated physical problems. Some examples of these problems are anxiety disorders, asthma, panic attacks, depression, anger, impotence, fears and phobias, grief, headaches, marriage problems, post Electro-Convulsive Therapy confusion, anxiety and memory loss, and post traumatic stress disorder (Vietnam and police service and child abuse and incest). The current undesirable behavior of a person provides connection of a current experience with a historical or more recent negative experience.

Historically, the primary mode of conducting psychotherapy for treatment of these problems has been by the use of one therapist with one patient or one or more therapists with a small group of patients. This mode of psychotherapy has been carried out mainly through verbal communication between therapists and patients. A significant drawback of relying primarily on verbal communication to conduct psychotherapy is that a large number of treatment sessions are needed to adequately deal with these problems. An unfortunate consequence of this is that the greater the overall quantity of time consumed in treatment the greater the cost and the fewer the number of persons that can be treated by a given population of therapists with proper qualification and clinical training. Another significant drawback is that some adults and many children are not verbal enough to successfully profit from verbal therapies. Also, many problems, through learned, do not respond well to verbal psychotherapy. These include problems such as asthma, allergies, chronic pain syndrome, attention deficit disorder, etc.

As a consequence, a need was recognized by the inventor psychologist herein for a different approach to psychotherapy for treatment of emotional problems and emotionally-aggravated physical problems which approach will overcome the above-described drawbacks without introducing new ones in their place. This need was substantially fulfilled by the psychotherapy apparatus and method of U.S. Pat. No. 5,219,322 which issued to the inventor herein on Jun. 15, 1993. The goal of the patented psychotherapy apparatus and method was to provide treatment of an undesirable emotional arousal of a patient through coordinated and controlled presentation of visual and auditory stimuli to the patient. In the apparatus, lights are so positioned and alternately switched that visual stimuli is observed by the stationarily-positioned patient at right and left extremes of the patient's range of lateral eye movement. Also, headphones are provided on the patient's ears and alternately switched between the patient's ears so that the auditory stimuli is alternately presented to the patient's ears with alternately switching of the visual stimuli. The physiological responses of the patient to the visual and auditory stimuli is monitored, and, in response thereto, the switching of the visual and auditory stimuli is controlled using a computer so as to elict a mental imagery of a negative experience of the patient and to eliminate undesirable emotional arousal evoked by the negative experience and substitute a positive experience reinforcing a desired behavior.

Continuing efforts made by the inventor herein with respect to the patented psychotherapy approach has led to the realization that by controlling and incorporating additional sources of stimulation over and above the visual and auditory stimuli disclosed in the above-cited patent, the purpose and scope of applications of the patented psychotherapy approach can be substantially expanded beyond merely the elimination of undesirable emotional response.

SUMMARY OF THE INVENTION

The present invention provides a psychotherapy apparatus and method for inputting and shaping new emotional and cognitive response patterns in a patient. The psychotherapy apparatus and method of the present invention achieves its expanded purpose and scope by combining and utilizing a plurality of separate, but funtionally related, components which can function together to restrict, select, control and focus the kinds of sensory stimuli reaching the patient for inputting and shaping the new emotional and cognitive response patterns in the patient.

Accordingly, the present invention is directed to a psychotherapy apparatus for inputting and shaping new emotional, physiological and cognitive response patterns in a patient. The psychotherapy apparatus basically comprises: means for isolating a patient from external stimuli; means for generating and presenting visual and auditory stimuli to the patient; means for delivering a flow of air to the patient for inhalation by the patient; means for controlling the temperature of the flow of air delivered to and inhaled by the patient to thereby control the temperature of the patient's hypothalamus; means for physiologically monitoring the patient and feeding back data about the patient; and means for receiving and responding to the feedback of patient data and for coordinating and timing the occurrence of the visual and auditory stimuli with the controlling of the temperature of the flow of air delivered to and inhaled by the patient to assist in the shaping of the new emotional, psychological and cognitive response patterns in the patient.

More particularly, the patient isolating means includes an enlosure in the form of an egg-shaped pod which is substantially soundproof and lightproof to reduce external stimuli reaching the patient and has a flat bottom and an entry and exit door to the enclosure on one side thereof, and a bed placed in the enclosure on the flat bottom thereof for supporting the patient in a low stimulus mode so as to further reduce the external stimuli reaching the patient. The visual stimuli generating and presenting means includes banks of lights located adjacent to the patient and adapted to operate in a coordinated fashion. The auditory stimuli generating and presenting means includes a sound generating device and sound listening earphones for use by the patient.

Further, the air flow delivering means is an elongated hollow tube for delivery of air flow to the nostrils of the patient in the enclosure for inhalation by the patient. The temperature controlling means includes flow generating means, such as a fan, operable to generate a flow of air, means for heating and cooling the flow of air received from the flow generating means, and a flow control valve disposed between the heating and cooling means and an entry end of the hollow tube and operable to control the proportion of air flow from the heating and cooling means into the entry end of the hollow tube and thereby control the temperature of the air flow delivered to the patient's nostrils. The heating and cooling means preferably is an electro-thermal heat pump coupled to a discharge side of the fan and having opposing heated and cooled heat exchangers for receiving the flow of air generated by the fan.

The psychotherapy apparatus also comprises: means for actuating extensor and flexor muscles of the patient concurrently with the receipt of other stimuli; means for delivering different selected aromas, such as by timed injections, into the flow of air being delivered to the patient; and patient push-button response means. The actuating means is a push-pull bar pivotally mounted in the enclosure in front of the arms of the patient for use by the patient in extending and flexing the muscles of the arms as other stimuli is presented to the patient. The aroma delivering means is an aromatic generation unit operable to generate and inject on a timed basis a succession of impulses of different selected aromas into the air flow being delivered to the patient.

Furthermore, the stimuli occurrence coordinating and timing means includes an computer-implemented expert system which is employed to interview the patient and an interviewer of the patient and to evaluate the patient and develop a detailed treatment program to guide and track the patient's treatment. Also, the expert system is electrically connected to the visual and auditory stimuli generating and presenting means, air flow delivering means, temperature controlling means, aroma delivery means, physiological monitoring and data feedback means, patient push-button response means and patient muscle actuating means so as to control operation of such means in a desired predetermined coordinated fashion as determined by the patient's treatment program.

Also, the present invention is separately directed to an air flow generating and delivery device which comprises: air flow delivering means having spaced apart entry and discharge ends for receiving a flow of air from a first location and delivering the air flow to a second location; and air temperature controlling means. The air temperature controlling means includes means for generating the flow of air, an electro-thermal heat pump coupled to the air flow generating means and having opposing heated and cooled heat exchangers for receiving and respectively heating and cooling portions of the flow of air generated by the air flow generating means, and a flow control valve disposed between the heat pump and the entry end of the air flow delivering means and being operable to control the proportion of heated and cooled air flowing from the respective opposing heated and cooled heat exchangers of the heat pump into the entry end of the air flow delivering means and thereby control the temperature of the air flow delivered to the discharge end of the air flow delivering means.

Further, the present invention is directed to a psychotherapy method for inputting and shaping new emotional, physiological and cognitive response patterns in a patient. The psychotherapy method basically comprises the steps of: isolating a patient from external stimuli; presenting visual and auditory stimuli to the patient; delivering a flow of air to the patient for inhalation by the patient; controlling the temperature of the flow of air delivered to and inhaled by the patient to thereby control the temperature of the patient's hypothalamus; physiologically monitoring the patient and feeding back data about the patient; and receiving and responding to the feedback of patient data and coordinating and timing the occurrence of the visual and auditory stimuli with the controlling of the temperature of the flow of air delivered to and inhaled by the patient to assist in the shaping of the new emotional, psychological and cognitive response patterns in the patient. Further, the psychotherapy method comprises the steps of: actuating extensor and flexor muscles of the patient concurrently with the receipt of other stimuli; delivering different selected aromas, such as by timed injections, into the flow of air being delivered to the patient; and providing a push-button for eliciting responses by the patient to the stimuli.

Also, the coordinating and timing includes operating a computer-implemented expert system to interview the patient and an interviewer of the patient and to evaluate the patient and develop a detailed treatment program to guide and track the patient's treatment. Also, the coordinating and timing also includes controlling in a desired predetermined coordinated fashion via the expert system, as determined by the treatment program of the patient, the presenting visual and auditory stimuli to the patient, delivering air flow to the patient, controlling the temperature of the air flow to the patient so as to control the temperature of the patient's hypothalamus, actuating the muscles of the patient, delivering of different selected aromas into the air flow and to the patient, responses made by the patient and monitoring of physiological parameters of the patient to assist in the shaping of the new emotional, physiological and cognitive response patterns in the patient.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which.

DETAILED DESCRIPTION OF THE INVENTION

Overview of Psychotherapy Apparatus

Overall, the psychotherapy apparatus of the present invention utilizes a plurality of separate, but functionally related, components which function together to restrict, select, control and focus the kinds of multiple sensory stimuli reaching a patient P for inputting and shaping new emotional, physiological and cognitive response patterns in the patient P. The complexity of the patient treatment procedures makes it imperative that the psychotherapy apparatus 10 utilize a computer-implemented expert system. The expert system orchestrates all of the components of the apparatus that generate audio sources, light patterns, auditory questions, aromas, visual displays and that monitor and feedback patient physiological data. Thus, the expert system controls all aspects of the patient treatment and responds to a treatment protocol based on an assessment of the individual patient (which is also done by the expert system).

More particularly, the expert system is employed to interview the patient and a human interviewer of the patient and to evaluate the patient and develop a detailed treatment program to guide and track the patient's treatment. This evaluation will be repeated periodically to update the treatment plan. The treatment plan will be an assemblage of stepwise treatment procedures, selected from a library of such protocols, to address each of the problems that have been enumerated for the patient.

During treatment, the patient will work their way through each treatment protocol that composes their treatment plan. Progress will be tracked by expert system analysis of the physiological monitors attached to the patient, by recorded questions that are asked of the patient and responded to by the patient's pressing buttons, as well as periodic reassessment by the computerized interview system and the human interviewer.

Preferred Embodiment of Psychotherapy Apparatus

Figure 5:
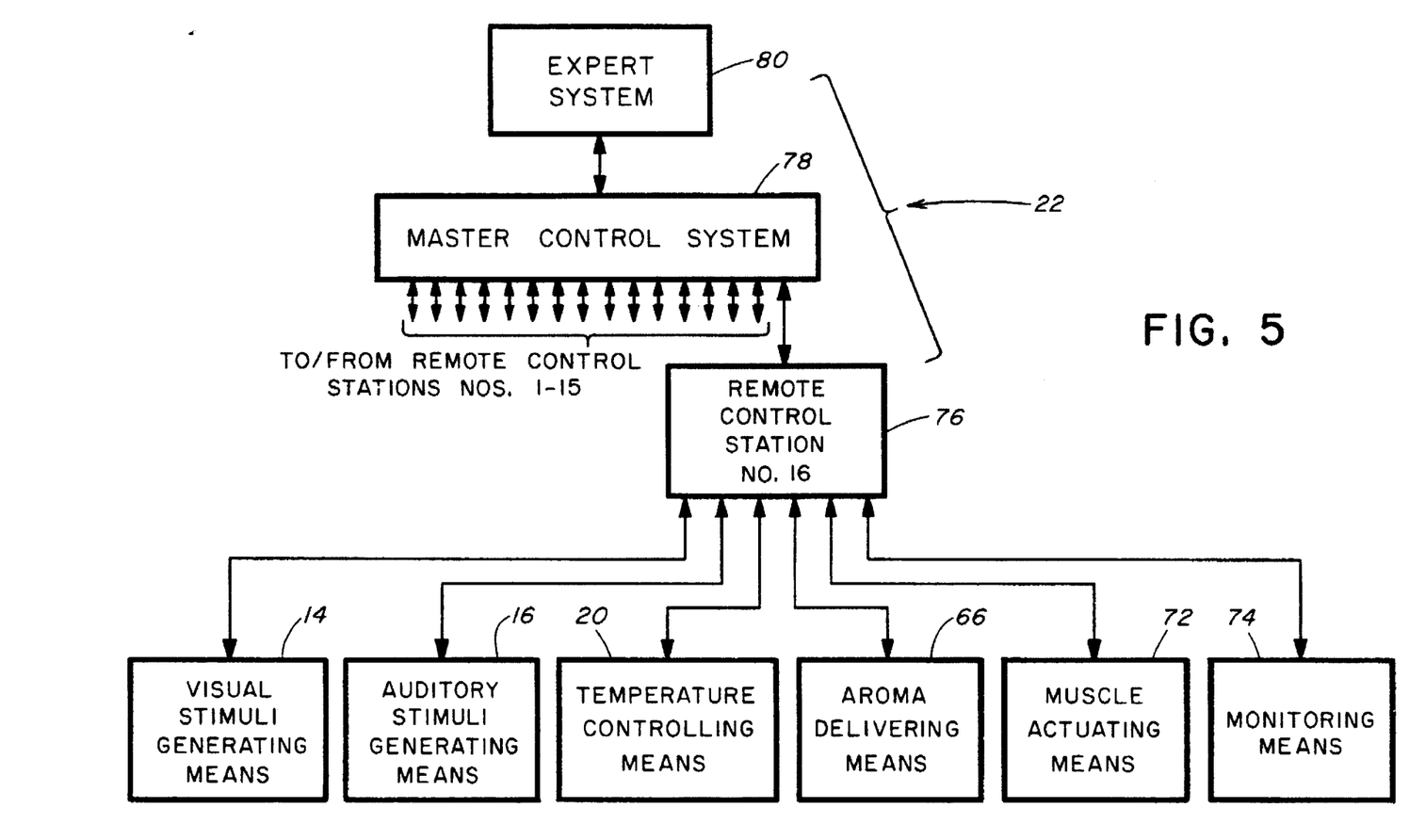
FIG. 5 is a block diagram of the various components of the apparatus for generating multiple stimuli delivered to a patient and for monitoring the patient and generating feedback of data about the patient, a remote control station for each patient, a computer-implemented expert system for controlling operation of each remote control station via the coordination of a master control station connected between the expert system and each remote control station.

Referring to the drawings and particularly to FIG. 1–5, there is illustrated a preferred embodiment of the psychotherapy apparatus of the present invention, generally designated 10, for carrying out these patient treatment procedures in accordance with a preferred embodiment of a psychotherapy method of the present invention. The psychotherapy apparatus 10 basically includes means 12 for isolating the patient P from external stimuli, means 14, 16 for generating and presenting visual and auditory stimuli to the patient P, means 18 for delivering a flow of air to the patient P for inhalation by the patient P, and means 20 for controlling the temperature of the flow of air delivered to and inhaled by the patient P to thereby control the temperature of the patient's hypothalamus. Referring also to FIG. 5, the psychotherapy apparatus 10 also basically includes means 22 for coordinating and timing the occurrence of the visual and auditory stimuli with the controlling of the temperature of the flow of air delivered to and inhaled by the patient P as well as of other stimuli, described later on, being delivered to the patient P.

Figure 1:
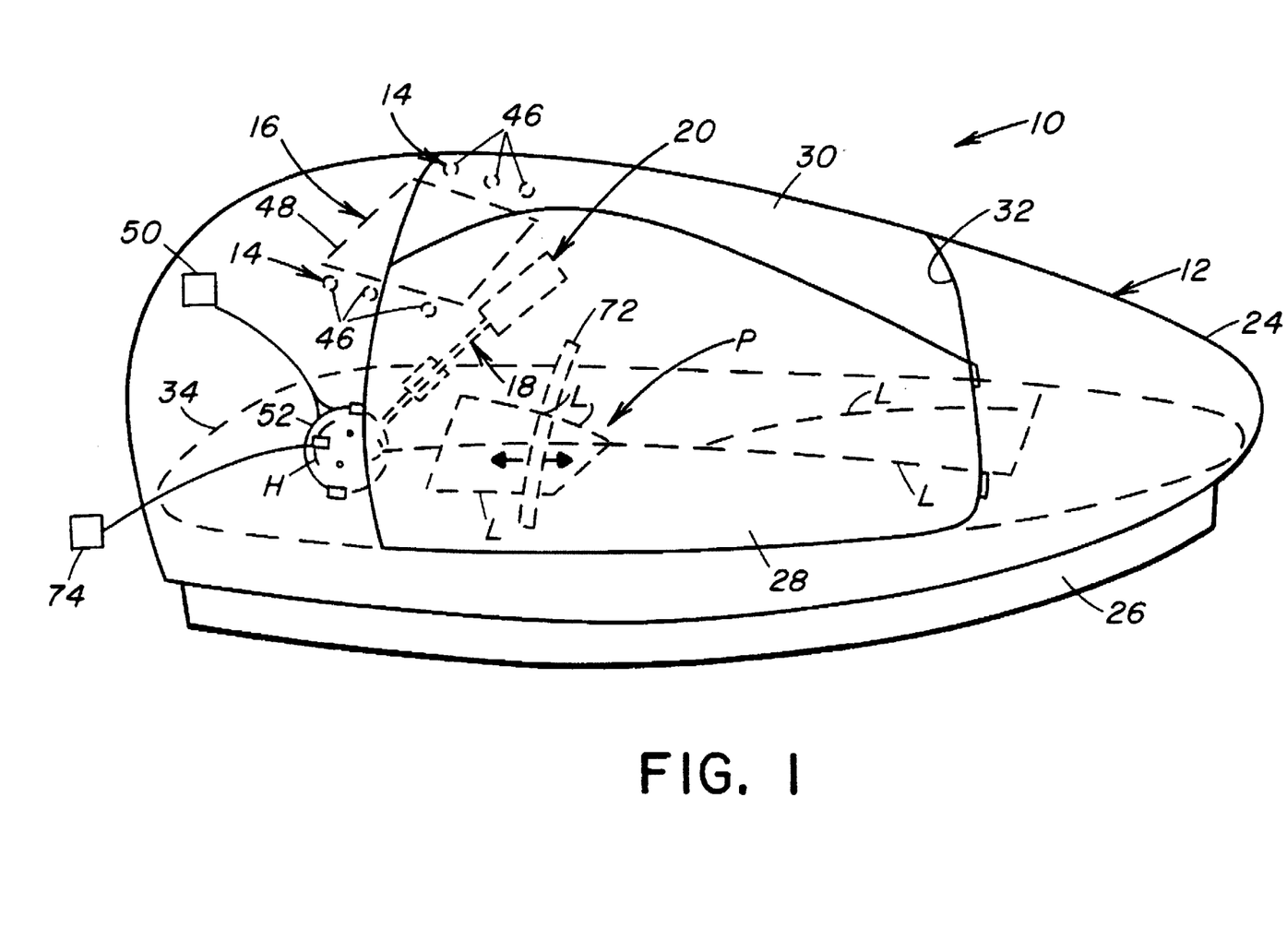
FIG. 1 is a diagrammatic view of a preferred embodiment of a psychotherapy apparatus of the present invention.
Figure 2:
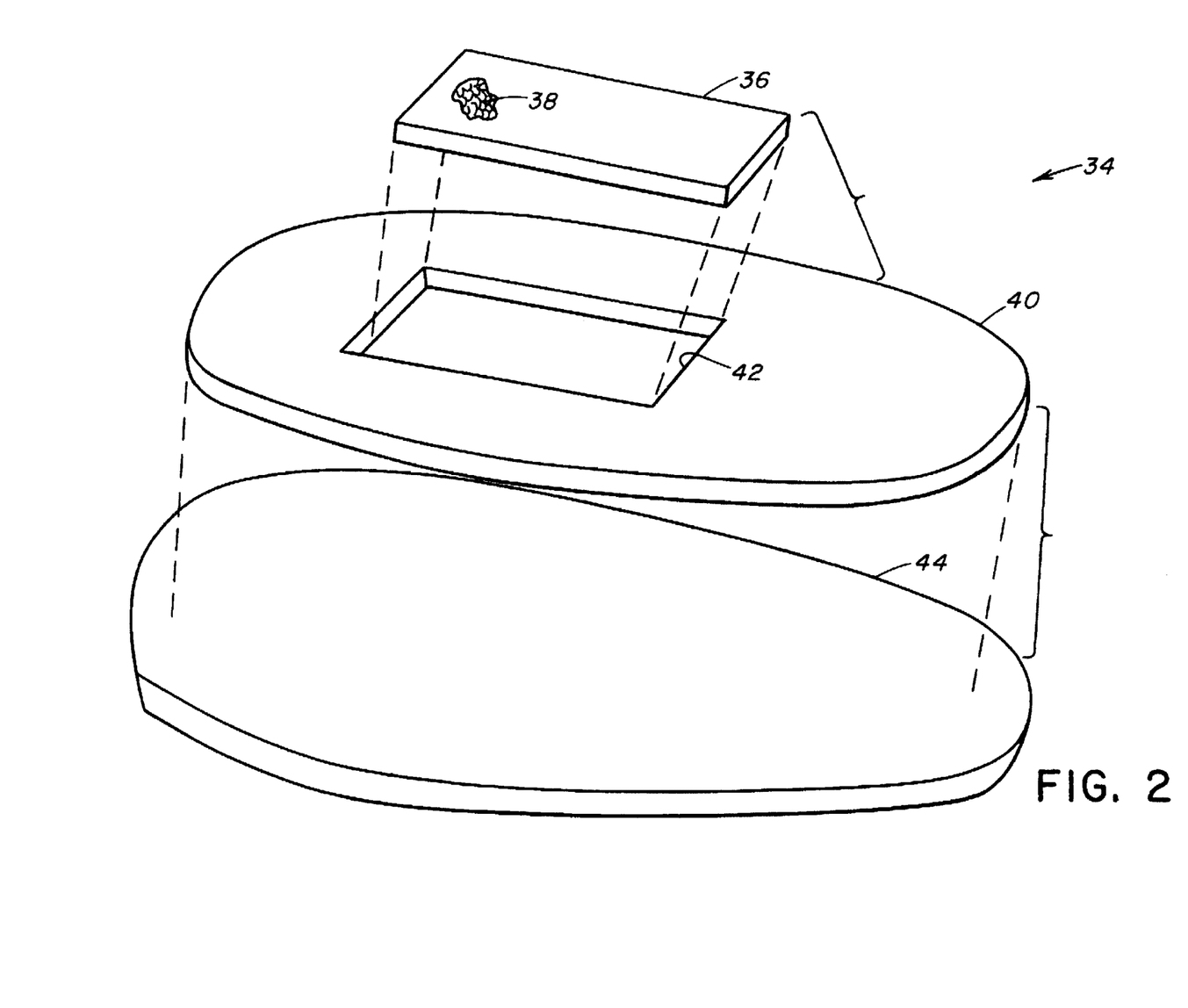
FIG. 2 is an exploded diagrammatic view of a platform employed in an enclosure of the apparatus of FIG. 1.

In a practical implementation of the psychotherapy apparatus 10 as diagrammatically depicted in FIGS. 1 and 2, the patient isolating means 12 more particularly includes an enlosure 24 in the form of an egg-shaped pod which is substantially soundproof and lightproof to reduce external stimuli of various types reaching the patient P in the enclosure 24. The enclosure 24 has a flat bottom 26, a entry and exit door 28 hinged on a side of the enclosure 24, and a removable top cover or hatch 30 overlying a top opening 32 in the enclosure 24. The hatch 30 provides access to an upper equipment compartment separate from the patient's compartment. Also, the patient isolating means 12 includes a bed 34 placed in the enclosure 24 on the flat bottom 26 thereof for supporting the patient P when lying down on the bed 34. The bed 34 preferably is constructed with an upper flexible bag 36, filled with particles 38 of small size, such as beans, pellets or beads, an outer pad 40 having a central cavity 42 receiving the upper bag 36, and a lower mattress 44 supporting both the upper bag 36 and outer pad 40. The upper bag 36 is somewhat flattened preferably into a rectangular shape and has a size, for example, of about two inches in thickness, four feet in length and twenty-two inches in width. The outer pad 40 preferably is made of a relatively soft compressible foam having a rounded ring shape surrounding the upper flat bag 36. The lower mattress 44 preferably is made of a relatively stiff foam rubber supporting the upper flat bag 36 and outer pad 40 such that with the patient's head H and trunk T supported on the upper flat bag 36 the patient's limbs L extend outwardly over and are supported by the outer pad 40. Preferably, the foam material of the lower mattress 44 is firmer or stiffer than that of the outer pad 40. The firmness of the bed 34 is controlled by varying the density of the beans. Denser beans provide more support by means of the principle of flotation and thereby provide a firmer feel to the bed. Less dense beans provide more of their support through the displacement principle and thus provide a softer feel.

Thus, the enclosure 24 and bed 34 are constructed so as to support the patient P in a relatively "low stimulus mode", that is, in such way as to restrict and reduce external stimuli from reaching the patient P that would dilute the effect of the selected stimuli emanating from the operation of the apparatus 10 on the the senses of the patient P. Restriction of sensory intake of the patient P to only selected stimuli makes their effects on the patient P much more powerful and therapeutic.

The visual and auditory stimuli generating and presenting means 14, 16 of the psychotherapy apparatus 10 of the present invention is similar to that used in the apparatus disclosed in the inventor's previous above-cited patent. Thus, the disclosure of U.S. Pat. No. 5,219,322 is hereby incorporated herein by reference thereto. The visual stimuli generating and presenting means 14 basically includes banks of lights 46 and a visual display 48 located between the banks of lights 46 with both being placed within the line of vision of the patient P and adapted to operate in a coordinated fashion. Also, the auditory stimuli generating and presenting means 16 basically includes a device 50 for generating sound and a pair of earphones 52 for the patient P to listen to the sound. The sound generating device 50 and the headphones or earphones 52 are preferably used in coordination with the bank of lights 46 and display 48. The lights 46 can be alternated from side-to-side between the opposite banks thereof as the sound is alternated between the ears of the patient. By way of example, the sound generating device 50 can be an audio cassette player operable to play an audio tape containing pre-recorded sound, such as music and verbal messages. Additionally, the device 50 can include a microphone to permit the making of live verbal message. The human operator as well as the patient is equipped with a microphone and headphone which allows the patient and operator to communicate with one another. The patient's microphone is equipped with a vox circuit to prevent transmission to the operator of extraneous sounds occurring in the pod. Also, the sound generating device 50 should be capable of generating phase shifts and Doppler frequency shifts as the sound moves back and forth between the ears of the patient.

Figures 3, 4:
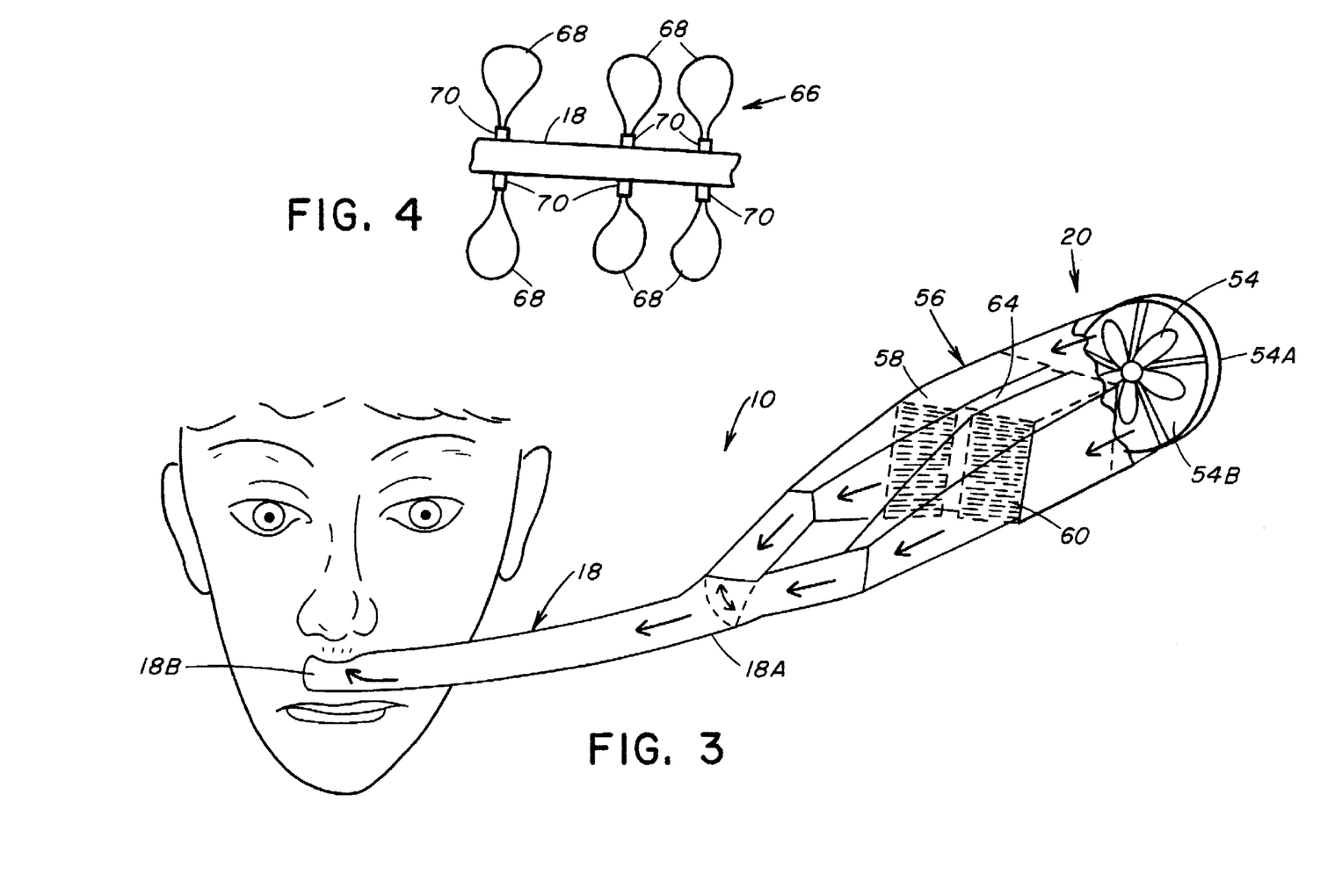
FIG. 3 is a diagrammatic view of a temperature control device of the apparatus employed for controlling the temperature of a flow of air delivered to a patient to thereby control the temperature of the patient's hypothalamus.
FIG. 4 is a diagrammatic view of a smell injecting device of the apparatus incorporated in an air flow delivery tube of the temperature control device.

Referring to FIGS. 1 and 3, the air flow delivering means 18 of the apparatus 10 is an elongated hollow tube 18, such as a ½ inch neoprene tube, having opposite entry and discharge ends 18A, 18B for receiving a flow of air at the entry end 18A and for delivery of the air flow from the discharge end 18B to the nostrils of the patient P lying on the bed 34 in the enclosure 24 for inhalation by the patient P. The discharge end 18B of the hollow tube 18 rests on the patient's upper lip and aims the air flow to just below the patient's nostrils.

The temperature controlling means 20 of the apparatus 10 is provided to control temperature of the patient's hypothalamus by controlling the temperature of the flow of air delivered through the hollow tube 18 to patient and inhaled by the patient P. The hypothalamus is a brain stem structure which is crucial in the control of many functions of the patient, such as body temperature, emotions, release of neuro transmitters, aggression, pain perception, eating, sex, etc. The temperature of the hypothalamus itself has clear, well documented, effects on all of these functions. The hypothalamus is cooled by its arterial blood supply, via a rather complicated heat exchanger process. Briefly stated, as a person inhales through the nose, venous blood in the nasal membrane is cooled by evaporation. This venous blood flows to the cavernous sinus artery, which is the only place in the body where an artery passes in the interior of a vein. This concentric arrangement lets the evaporatively cooled venous blood cool the arterial blood it surrounds. Conveniently, this whole process happens just before the arterial blood enters the hypothalamus. The temperature of the hypothalamus is modified by the temperature of the arterial blood flowing into it. The supplying of warm air to the patient's nostrils will diminish the evaporative cooling of the venous blood in the nasal membrane, whereas the supplying of cool air will augment it. With respect to the emotional state of the patient, if cool air is supplied the patient's mood is improved, whereas mood is degraded when warm air is supplied.

More particularly, the temperature controlling means 20 includes air flow generating means preferably in the form of air flow generating means preferably in the form of a fan 54 having an intake side 54A and a discharge side 54B and being operable to generate a flow of air from the discharge side 54B, air heating and cooling means preferably in the form of an electro-thermal heat pump 56 coupled to the discharge side 54B of the fan 54 and having opposing heated and cooled heat exchangers 58, 60 for receiving and heating and cooling respective portions of the air flow from the discharge side 54B of the fan 54, and a flow control valve 62, such as an electronically-controlled valve, disposed between and connected to the heat pump 56 and the entry end 18A of the hollow tube 18 and operable to control the proportion of heated and cooled air flowing from the respective opposing heated and cooled heat exchangers 58, 60 of the heat pump 56 into the entry end 18A of the hollow tube 18 and from the discharge end 18B thereof and thereby control the temperature of the air flow delivered to the patient's nostrils. The heat pump 56 also includes a Peltier junction 64 coupled between the heated and cooled heat exchangers 58, 60 and being electrically operable in a known manner to maintain the heated heat exchanger 58 approximately 100° C. hotter than the cooled heat exchanger 60. It should be understood that, while forming no part of the present invention and thus not necessary to be shown in the drawings, the operation of the Peltier junction 64 necessitates that there always be some proportion of constant flow of air over the heated heat exchanger 58 Peltier junction 64 to dissipate the heat removed from the cooled heat exhanger 60 to maintain it cool and to dissipate the heat from electrical operation of the Peltier junction 64. This extra heated air flow from the Peltier junction 64 is merely "leaked" into the room and does not affect patient treatment.

Referring to FIGS. 1 and 4, the psychotherapy apparatus 10 preferably also includes means 66 for delivering different selected aromas into the flow of air delivered to the patient P. The olfactory bulb goes directly into the lymbic system of the brain. The lymbic system is primarily concerned with emotions. So, aromas are very powerful stimulators of emotions. The aroma delivering means 66 is an aromatic generation unit having a plurality of dispensers 68 containing different selected aromas. Each dispenser 68 has an injection head 70 thereon connected to the air flow delivery tube 18. The injection heads 70 are electrically operable to inject into the air flow in the tube 18, for delivery to the patient P preferably on a timed basis (as opposed to a continuous basis), an impulse of a selected one of different aromas provided by the dispensers 68. Thus, the patient is presented with selections from a "library" of aromas that stimulate memories and emotions. Some of these emotional responses are based on the individual's unique prior experience. Other responses are based on inherited "domain specific" patterns.

Still further, the psychotherapy apparatus 10 also includes means 72 for actuating extensor and flexor muscles of the patient P concurrently with the receipt of other stimuli from the aforementioned components of the apparatus 10. The actuating means 72 of the apparatus 10 preferably takes the form of an adjustable push-pull bar 72 pivotally mounted in the enclosure 24 in front of the arms A of the patient P for use by the patient P, for instance, in flexing the bicep muscles and extending the tricep muscles of the arms as other stimuli is presented to the patient. The bar 72 is preferably mounted at approximately sternum level about one foot in front of the patient P. There is probably nothing particularly therapeutic about pushing or pulling on the bar 72 by itself. What is important is how it is coordinated with other stimuli.

The reason for using the push-pull actuating means 72 with other stimuli is that thoughts the patient has when actuating flexor (biceps) muscles by pulling toward the body are given a more positive valence whereas thoughts the patient has when actuating extensor (tricep) muscles by pushing away from the body are given a more negative valence. In other words, people pull things toward them that they like and push away things they dislike. Thus, the patient would be instructed to push or pull on the bar 72 concurrently with being asked to think about something or while being sent auditory or visual stimuli.

Also, the causality goes both directions; the opposite is also equally true. The things people push away become the things they dislike and the things people pull toward them become the things they like. Many other extensor and flexor muscles would also work, however, the biceps and triceps muscles are convenient to work with. Also sensors, such as strain gauges or the like, could be attached to the bar to measure stress/movement on the bar on all axes. This would measure spontaneous movement of the push-pull bar 72 in response to changing psychological and physical states. This allows assessment of the patient's evaluation of these states.

Referring to FIG. 5, the psychotherapy apparatus 10 also includes monitoring means 74, preferably although not exclusively in the form of an electroencephlograph (EEG), to physiologically monitor the patient and feedback data to the stimuli occurrence coordinating and timing means 22 to assist in the shaping of the new emotional and cognitive response patterns in the patient. The EEG is one useful tool for monitoring and assisting in the conditioning of attentional, emotional and cognitive states. Shaping would be driven by the respondent and/or operant presentation of the consequatory class of stimuli with the desired EEG pattern or pattern stimuli.

There are other types of transducer devices which are equally useful tools for monitoring different physiological parameters of the patient and obtaining feedback information to the coordinating and timing means 22. For example, electromyography can be used for monitoring the zygomatic (jaw) and frontalis (forehead) muscles and appropriate transducer devices can be used for monitoring peripheral temperature (finger), Galvanic skin resistance (changing electrical resistance on the fingers), and pulse. Other parameters which can be monitored are respiration, gastric motility, blood pressure, papillary response, etc.

Referring to FIG. 5, there is shown the stimuli occurrence coordinating and timing means 22 of the apparatus 10 for controlling in a meaningful way the various above-described components of the apparatus 10 for generating the multiple stimuli delivered to a patient and for monitoring data about the patient. The coordinating and timing means 22 takes the form of a remote control station 76 for each patient, a master control station 78 connected to each remote control station 76, and a computer-implemented expert system 80 for controlling operation of each remote control station 76 via the coordination of the master control station 78 connected between the expert system 80 and each remote control station 76. In the present embodiment, there can be up to sixteen remote control stations 76 serviced by one expert system 80 through one master control station 78.

The expert system 80 preferably includes two computer-implemented subsystems. The first subsystem is a pattern recognition/classifier type which functions to categorize the patterns of physiological data received from the patients. The second subsystem is a rule based expert type. The categories of the first subsystem, the pattern recognition/classifier type, serve as inputs to the second subsystem, the rule based expert type.

As seen in FIG. 5, the computer-implemented expert system 80 is electronically connected to the various different stimuli generating means and patient data monitoring means associated with each patient via the master control station 78 and a separate remote control station 76 associated with a respective one enclosure 24 and connected to the master station 78 for each patient being treated. As described before, the different patient stimuli connected to each remote control station 76 include the banks of lights 46 and sound generating device 50 of the visual and auditory stimuli generating and presenting means 14, 16, the air flow control valve 62 of the temperature controlling means 20, the injection heads 70 of the aroma delivery means 66, and the muscle actuating means 72. The expert system 80 causes the operation of such various multiple stimuli means in a desired predetermined coordinated fashion as determined by the patient's treatment program.

More particularly, the expert system 80 basically operates in accordance with the following steps.

First: A human therapist interviews the patient.

Second: The expert system interviews the patient and also interviews the therapist about the patient.

Third: The expert system then combines data from the interviews and develops a patient problem list based on the interviews.

Fourth: The expert system selects a set of treatment protocols from a protocol library residing in the computer in which the expert system also resides. These selected protocols will address the elements of the various problems in the patient problem list. The treatment protocol is a set of rules which describe the logical and temporal relationship of patient and operator inputs with patient stimuli. The protocol library is a set of these protocols designed to address all the patient problems that the apparatus 10 is anticipated to encounter.

Fifth: The patient selects a problem from the problem list to work on in the current session. The expert system selects the particular treatment protocol which correspond to the problem selected by the patient.

Sixth: The expert system administers the treatment in accordance with the rules of the selected protocol(s) by causing the generation in a coordinated fashion of the various patient stimuli which include: visual, auditory (sound, music verbal instructions generated by computer or a human operator), hypothalamus cooling or heating, extensor/flexor muscle, olfactory, kinesthetic, and aromatic stimuli.

Seventh: The expert system monitors patient data via patient button responses to digitized and operator speech presented questions and physiological measures (which responses as they are received by the expert system are classified by the expert system into meaningful categories). Patient data is composed of patient physiological measures (electroencephalogram, electromyogram, Galvanic Skin Response, respiration, pulse, blood pressure, aortic sinus pulse rhythm changes, peripheral and central temperature changes, etc.), button presses, behavorial responses such as pushing or pulling on the bar and verbal responses.

Eighth: The expert system adjusts the generation of the stimuli in response to patient data and also according to the rules of the protocol(s). This may include moving to the next problem on the patient problem list.

Ninth: The expert system stores patient problem list progress and an "audit trail" of the treatment and responses at the end of each session so that the next session can begin where the last one left off.

Tenth: Subsequent sessions typically begin with the Fifth step. Every few sessions the procedure is restarted at the First step.

From the above-described steps, it can be understood that the expert system 80 controls all facets of a patient's treatment, from interviewing each patient and also the therapist of the patient through evaluating the patient and developing a detailed treatment program to administering the treatment program and tracking the patient's treatment. The evaluation of the patient will be repeated periodically to update the treatment plan.

The treatment plan is an assemblage of stepwise treatment procedures, selected from a library of such protocols, to address each of the problems that have been enumerated for the patient. The protocols control all of the variables the apparatus 10 is capable of: (1) digitized speech for questions and instructions; (2) changing light and sound patterns; (3) switching different sources of sound such as CD players, cassette tapes, microphone, digitized speech of the hard drive; (4) monitoring and interpreting physiological changes in the patient; (5) monitoring and interpreting button presses on the part of the patient; (6) tracking progress, success and failure of progression through treatment protocols, patient knowledge base; (7) visual and olfactory stimuli presentation; (8) tactile and kinesthetic stimuli presentation; and (9) visual and auditory subliminals, dichotic listening, etc.

Thus, during treatment sessions the patient will work their way through each treatment protocol that composes their treatment plan. Progress is tracked by expert system analysis of the physiological monitors attached to the patient, by recorded questions that are asked of the patient and responded to by the patient's pressing buttons, as well as periodic reassessment by the computerized interview system and human interviewer.

There are two conceptual categories regarding stimuli: those that carry content and those that provide consequences. Providing operant and/or respondent relationships between these classes of stimuli via electronic, computer and expert system control is what makes it possible to manage and run this multi-media, multi-modality sensory stimulation system.

In summary, the basic operative steps performed by the above-described psychotherapy apparatus of the present invention for inputting and shaping new emotional, physiological and cognitive response patterns in a patient, which constitute the psychotherapy method of the present invention, are as follows: isolating the patient from external stimuli; presenting visual and auditory stimuli to the patient; delivering a flow of air to the patient for inhalation by the patient; controlling the temperature of the flow of air delivered to and inhaled by the patient to thereby control the temperature of the patient's hypothalamus; monitoring physiological parameters of the patient and feeding back data about the patient; and receiving and responding to the feedback of patient data and coordinating and timing the occurrence of the visual and auditory stimuli with the controlling of the temperature of the flow of air delivered to and inhaled by the patient to assist in the shaping of the new emotional, physiological and cognitive response patterns in the patient.

More particularly, the receiving and responding to feedback of patient data and the coordinating and timing of the occurrence of stimuli includes operating the computer-implemented expert system to interview the patient and a human interviewer of the patient and to evaluate the patient and develop a detailed treatment program to guide and track the patient's treatment. Also, the coordinating and timing includes controlling in a desired predetermined coordinated fashion via the expert system, as determined by the treatment program of the patient, the presenting visual and auditory stimuli to the patient, the delivering air flow to the patient and the controlling the temperature of the air flow to the patient so as to control the temperature of the patient's hypothalamus. Other operative steps are as follows: actuating extensor and flexor muscles of the patient concurrently with the receipt of other stimuli; and delivering different selected aromas into the flow of air being delivered to the patient.

For example, with the patient lying in the soundproof enclosure, images projected on the visual screen of the display can be reinforced or punished with hypothalamus cooling or heating by using the temperature controlling means as well as with injection of aromas by using the aroma delivering means. These procedures can be performed on the patient with the patient outside of the state of consciousness by using subliminal visual or auditory messages by using the visual and auditory stimuli generating means that are reinforced or punished by smell or hypothalamus temperature changes or by super or subliminal speech or music. The patient is much more responsive to these procedures because of the dream-like state induced by the moving lights and sound. The individual patient's responsiveness to different variations in these procedures can be tracked by the physiological monitoring. This will allow the expert system to learn what is effective for the individual patient and respond accordingly.

It is thought that the present invention and its advantages will be understood from the foregoing description and it will be apparent that various changes may be made thereto without departing from the spirit and scope of the invention or sacrificing all of its material advantages, the form hereinbefore described being merely preferred or exemplary embodiment thereof.

I claim:

1. A psychotherapy apparatus for inputting and shaping new emotional, psychological and cognitive response patterns in a patient, said apparatus comprising:
    (a) means for isolating a patient from external stimuli;
    (b) means for presenting visual and auditory stimuli to the patient;
    (c) means for delivering a flow of air to the proximity of nostrils of the patient for inhalation of the flow of air by the patient;
    (d) means for controlling the temperature of the flow of air delivered to the proximity of the patient's nostrils and inhaled by the patient to thereby control the temperature of the patient's hypothalamus;
    (e) means for physiologically monitoring the patient and feeding back data about the patient; and
    (f) means for receiving and responding to the feedback of patient data and for coordinating and timing the occurrence of the visual and auditory stimuli with the controlling of the temperature of the flow of air delivered to the proximity of the patient's nostrils and inhaled by the patient to assist in the shaping of the new emotional, psychological and cognitive response patterns in the patient.

2. The apparatus of claim 1 wherein said patient isolating means includes an enlosure in the form of an egg-shaped pod having a construction substantially soundproof and light-proof to reduce external stimuli reaching the patient.

3. The apparatus of claim 2 wherein said enclosure has a flat bottom and an entry and exit door on one side thereof.

4. The apparatus of claim 2 wherein said patient isolating means also includes a bed placed in said enclosure for supporting the patient in a low stimulus mode so as to further reduce external stimuli reaching the patient.

5. The apparatus of claim 1 wherein said visual stimuli generating and presenting means includes banks of lights located adjacent to the patient and adapted to operate in a coordinated fashion.

6. The apparatus of claim 1 wherein said auditory stimuli generating and presenting means includes a sound generating device and sound listening earphones.

7. The apparatus of claim 1 wherein said air flow delivering means is an elongated hollow tube having an entry end and a discharge end, said discharge end being located near the nostrils of the patient for delivery of air flow to the nostrils of the patient for inhalation by the patient.

8. The apparatus of claim 7 wherein said temperature controlling means includes:
    means for generating a flow of air;
    heating and cooling means coupled to said air flow generating means for receiving and heating and cooling respective portions of the flow of air generated; and
    a flow control valve disposed between said heating and cooling means and said entry end of said hollow tube and operable to control the proportion of heated and cooled air flowing from said heating and cooling means into said entry end of said hollow tube and thereby control the temperature of the air flow delivered from said discharge end of said hollow tube to the patient's nostrils.

9. The apparatus of claim 8 wherein:

said air flow generating means is a fan having an inlet side and a discharge side; and said heating and cooling means is an electro-thermal heat pump coupled to said discharge side of said fan and having opposed heated and cooled heat exchangers for receiving and heating and cooling respective portions of the flow of air generated by said fan.

10. The apparatus of claim 1 wherein said means for receiving and responding to feedback of patient data and for coordinating and timing the occurrence of stimuli includes a computer-implemented expert system operable to interview the patient and a therapist of the patient and to evaluate the patient and develop a detailed treatment program to guide and track the patient's treatment, said expert system also being connected to said visual and auditory stimuli generating and presenting means, air flow delivering means and temperature controlling means so as to control operation of the same in a desired predetermined coordinated fashion as determined by said treatment program of the patient.

11. The apparatus of claim 1 further comprising:

(g) means for actuating extensor and flexor muscles of the patient concurrently with the receipt of other stimuli.

12. A psychotherapy apparatus for inputting and shaping new emotional, psychological and cognitive response patterns in a patient, said apparatus comprising:

(a) means for isolating a patient from external stimuli;

(b) means for presenting visual and auditory stimuli to the patient;

(c) means for delivering a flow of air to the patient for inhalation by the patient;

(d) means for controlling the temperature of the flow of air delivered to and inhaled by the patient to thereby control the temperature of the patient's hypothalamus;

(e) means for physiologically monitoring the patient and feeding back data about the patient;

(f) means for receiving and responding to the feedback of patient data and for coordinating and timing the occurrence of the visual and auditory stimuli with the controlling of the temperature of the flow of air delivered to and inhaled by the patient to assist in the shaping of the new emotional, psychological and cognitive response patterns in the patient; and (g) means for actuating extensor and flexor muscles of the patient concurrently with the receipt of other stimuli, said actuating means being a push-pull bar pivotally mounted in said patient isolating means in front of the arms of the patient for use by the patient in extending and flexing the muscles of the arms as other stimuli is presented to the patient.

13. The apparatus of claim 1 further comprising:

(g) means for delivering different aromas into the flow of air being delivered to the patient.

14. The apparatus of claim 13 wherein said aroma delivering means is an aromatic generation unit operable to generate and inject on a timed basis a succession of impulses of different selected aromas into the air flow being delivered to the patient.

15. A air flow generating and delivery device, comprising:

(a) air flow delivering means having spaced apart entry and discharge ends for receiving a flow of air from a first location and delivering the air flow to a second location; and (b) air temperature controlling means including (i) means for generating the flow of air, (ii) an electro-thermal heat pump coupled to said air flow generating means and having opposing heated and cooled heat exchangers for receiving and respectively heating and cooling portions of the flow of air generated by said air flow generating means, and (iii) a flow control valve disposed between said heat pump and said entry end of said air flow delivering means and being operable to control the proportion of heated and cooled air flowing from said respective opposing heated and cooled heat exchangers of said heat pump into said entry end of said air flow delivering means and thereby control the temperature of the air flow delivered to said discharge end of said air flow delivering means.

16. The device of claim 15 wherein said air flow delivering means is an elongated flexible hollow tube.

17. The device of claim 15 wherein said air flow generating means is a fan having an inlet side and a discharge side, said heat pump being connected in communication with said discharge side of said fan.

18. A psychotherapy method for inputting and shaping new emotional, physiological and cognitive response patterns in a patient, said method comprising the steps of:

(a) isolating a patient from external stimuli;

(b) presenting visual and auditory stimuli to the patient;

(c) delivering a flow of air to the proximity of nostrils of the patient for inhalation of the flow of air by the patient;

(d) controlling the temperature of the flow of air delivered to the proximity of the patient's nostrils and inhaled by the patient to thereby control the temperature of the patient's hypothalamus;

(e) physiologically monitoring the patient and feeding back data about the patient; and (f) receiving and responding to feedback of patient data and coordinating and timing the occurrence of the visual and auditory stimuli with the controlling of the temperature of the flow of air delivered to the proximity of the patient's nostrils and inhaled by the patient to assist in the shaping of the new emotional, psychological and cognitive response patterns in the patient.

19. The method of claim 18 further comprising the step of:

(g) actuating extensor and flexor muscles of the patient concurrently with the receipt of other stimuli.

20. The method of claim 18 further comprising the step of:

(g) delivering different selected aromas into the flow of air being delivered to the patient.

21. The method of claim 18 wherein said receiving and responding to feedback of patient data and said coordinating and timing the occurrence of stimuli includes operating a computer-implemented expert system to interview the patient and a therapist of the patient and to evaluate the patient and develop a detailed treatment program to guide and track the patient's treatment.

22. The method of claim 21 wherein said receiving and responding to feedback of patient data and said coordinating and timing the occurrence of stimuli also includes controlling in a desired predetermined coordinated fashion via said expert system, as determined by said treatment program of the patient, said presenting visual and auditory stimuli to the patient, said delivering air flow to the patient and said controlling the temperature of the air flow to the patient to control the temperature of the patient's hypothalamus.

23. The method of claim 21 further comprising the steps of:

(g) actuating extensor and flexor muscles of the patient concurrently with the receipt of other stimuli; and (h) delivering different aromas into the flow of air being delivered to the patient.

24. The method of claim 23 wherein said receiving and responding to feedback of patient data and said coordinating and timing the occurrence of stimuli also includes controlling in a desired predetermined coordinated fashion via said expert system, as determined by said treatment program of the patient, said presenting visual and auditory stimuli to the patient, said delivering air flow to the patient, said controlling the temperature of the air flow to the patient to control the temperature of the patient's hypothalamus, said actuating of said muscles and said delivering said selected aromas.

* * * * *